United States Patent [19]

Schmidt et al.

[11] Patent Number: 4,486,435

[45] Date of Patent: Dec. 4, 1984

[54] SPRAY-DRIED VITAMIN POWDERS USING HYDROPHOBIC SILICA

[75] Inventors: Douglass N. Schmidt, Grosse Ile; Jeffrey L. Finnan, Southgate; Rudolph E. Lisa, Grosse Ile, all of Mich.

[73] Assignee: BASF Wyandotte Corporation, Wyandotte, Mich.

[21] Appl. No.: 494,990

[22] Filed: May 16, 1983

[51] Int. Cl.$^3$ .................. A61K 31/525; A61K 47/00; A61K 31/595; A61K 31/365
[52] U.S. Cl. ................................. 424/252; 424/201; 424/236; 424/237; 424/255; 424/263; 424/266; 424/280; 424/284; 424/332; 424/344; 424/357
[58] Field of Search ............... 424/252, 201, 236, 237, 424/255, 263, 266, 280, 284, 332, 344, 357

[56] References Cited

U.S. PATENT DOCUMENTS 3,116,204  12/1963  Siegel et al. ................... 424/252
3,959,472   5/1976  Cannalonga et al. ............ 424/252

FOREIGN PATENT DOCUMENTS 791684   8/1968  Canada ........................... 424/252
2811222  9/1979  Fed. Rep. of Germany ...... 424/252

OTHER PUBLICATIONS

Chem. Abst. 81, 36651z (1974)—Patil et al.
Chem. Abst. 84, 155570n (1976)—Grat et al.

Primary Examiner—Douglas W. Robinson
Attorney, Agent, or Firm—David L. Hedden; Joseph D. Michaels

[57] ABSTRACT

Encapsulated vitamin powders coated with a hydrophobic silica have improved free-flowing properties making these powders more suitable for direct tableting preparation.

10 Claims, No Drawings

SPRAY-DRIED VITAMIN POWDERS USING HYDROPHOBIC SILICA

BACKGROUND OF THE INVENTION

1. Field of the Invention

This invention relates to non-agglomerated, free-flowing, vitamin powders containing a coating of hydrophobic silica.

2. Description of the Prior Art

Heretofore, agglomerated vitamin-containing powders have been prepared containing a coating of an absorbent material such as silicic acid by spray-drying a mixture of an aqueous vitamin slurry or emulsion in the presence of such a dry particulate absorbent material. Examples of such powders are disclosed in U.S. Pat. No. 3,962,384; U.S. Pat. No. 3,959,472; U.S. Pat. No. 3,947,596; and U.S. Pat. No. 3,914,430.

It is conventional to spray-dry combinations of a medicament and a water-insoluble carrier such as calcium sulfate and dicalcium phosphate in the presence of a retarding agent so as to obtain solid, sustained release, pharmaceutical preparations, as disclosed in U.S. Pat. No. 3,632,739.

Vitamin-containing aqueous colloid beads have been prepared utilizing an aqueous solution of gelatin as an encapsulating agent. The aqueous gelatin coating around the vitamin is formed by spraying droplets of the aqueous gelatin-vitamin mixture into a cooling tower and collecting at the base of the tower in admixture with the resulting powder a water-absorbing powder such as powdered silica gel. The gelatin-coated vitamin is thereafter separated from the water-absorbing powder, as disclosed in U.S. Pat. No. 3,445,563.

The vitamin-containing powders of the prior art can be improved in free-flowing properties by spray-drying droplets of vitamin and encapsulating agent containing a water-insoluble carrier in the presence of a hydrophobic silica.

SUMMARY OF THE INVENTION

Encapsulated vitamin-containing, spray-dried, non-caking powders coated with a hydrophobic silica provide improved free-flowing powders as compared with those in the prior art.

The coated, free-flowing, non-hydroscopic, non-agglomerated vitamin powders suitable for the preparation of tablets by direct compression are prepared by:

spraying into a spray-dryer chamber droplets of a composition wherein said vitamin is present as a dispersion, a solution, or as an emulsion in an aqueous medium containing an encapsulating agent and wherein a water-insoluble carrier is also present in said aqueous medium, to produce a spray-dried powder which is dried in the presence of a dry particulate absorbent material. During spray-drying there is metered into said chamber, in a concentration of about 0.2 to about 2 percent by weight, based upon the weight of said spray-dried composition, a hydrophobic silica.

DETAILED DESCRIPTION OF THE INVENTION

Vitamin powders which are free-flowing and non-agglomerated can be prepared by the process of the invention. These powders are suitable for direct compression preparation of tablets and are particularly desirable in such procedures because of the improved flow properties and the reduction in sticking of the powder to the tablet press table, feed frame, and hopper.

It has been found that non-agglomerated, free-flowing, vitamin powders can be prepared by spray-drying a mixture of the vitamin present in an aqueous emulsion or in an aqueous dispersion containing an encapsulating agent or binder. Introducing a hydrophobic silica into the spray-drying chamber during the drying process, which is deposited upon the partially dried encapsulated particle as an outer shell, improves flowability. The particles of the aqueous composition containing a vitamin also can contain various adjuvents which are conventional in vitamin-containing powders. Such adjuvents can be lubricant compounds, binders, preservative compounds, fillers, and water-insoluble retarding agents. Said agents are resistant to disintegration in the gastro-intestinal tract. They are added in order to provide sustained release properties in the tablet prepared from the vitamin-containing powder.

The vitamin-containing powders of the invention can contain as the active vitamin ingredient thereof any suitable vitamin including a fat-soluble vitamin or mixture thereof, a water-soluble vitamin or mixture thereof, or mixtures of water-soluble and fat-soluble vitamins. For example, compositions containing such fat-soluble vitamins as vitamin A, vitamin D, vitamin E, vitamin K and mixtures thereof as well as compositions containing water-soluble vitamins such as those of the vitamin B complex, for instance, vitamins $B_1$, $B_2$, $B_6$, $B_{12}$ or vitamin C and mixtures thereof. The compositions of the invention can contain, for instance, such vitamins as niacinamide, salts of pantothenic acid such as calcium pantothenate, pantothenyl alcohol and mixtures of any of the foregoing vitamin ingredients.

As the encapsulating agent, filler or binder, generally any water-soluble starch, corn syrup, dextrin or pregelatinized starch which is at least partially soluble in water at ambient temperature can be employed in preparing the powder compositions of this invention. For example, there can be used as an encapsulating agent or binder the pregelatinized, modified and stabilized waxy maize starch which is marketed by the National Starch and Chemical Corporation under the trade name "Instant Clear Gel." In addition, pregelatinized corn starch marketed by the Hubinger Company under the trade name "OK Pre-Gel" can be used. Other binders suitable for use are pregelatinized food starch, refined from tapioca and marketed under the trade name "Instant Gel"; stable, modified amylopectin marketed under the trade name "Kosol"; a low viscosity tapioca dextrin marketed under the trade name "Crystal Gum"; dextrinized corn starch marketed under the trade name "Purity Glaze"; maltodextrin marketed under the trade name "Maltrin" M040 by Grain Processing Corporation. The encapsulating agent which is preferred for use in the invention as maltodextrin.

Other types of encapsulating agents or binders can be used such as water-soluble cellulose derivatives, for instance, hydroxyethyl cellulose or carboxymethyl cellulose, water-soluble plant gums such as gum arabic, gum tragacanth, alginates, gelatin and polyvinyl pyrrolidone.

A water-insoluble carrier may be used in the practice of this invention. These carriers must be non-toxic and inert to the other ingredients used in forming the vitamin powders of the invention. The carriers provide a nucleus upon which the vitamin and retarding agent, if used, may be carried so as to provide in the subsequent formation of a tablet an acceptable size and weight thereof. Suitable carriers can be inorganic or organic. Representative examples of suitable carriers are the alkaline earth metal sulfates such as calcium sulfate, the alkaline earth metal phosphates such as dicalcium phosphate, and organic carriers such as oyster shell flour, corn starch and rice starch. Carrier materials other than those mentioned above can be equally effective. It is not so much the chemical composition of the carrier but rather their physical properties which are critical in the preparation of the vitamin powders of the invention.

Of critical importance in the preparation of the vitamin powders of the invention is the utilization of ultra-fine particle size materials which are capable of coating the partially dried, encapsulated vitamin component. A coating of hydrophobic silica on the particles of the vitamin powders of the invention has been found to provide the desired properties. The hydrophobic silicas are substantially superior to those fine particle size silicas which are characterized as hydrophilic. The hydrophobic silicas are a special form of silica made from silica gel, precipitated silica or fumed silica by standard treatments known in the art. Such treatments involve the use of silanes or polysiloxanes to provide the desired hydrophobicity. It is also known to provide hydrophobic silicas by treatment of silica gel, precipitated silica or fumed silica with esterified coatings derived from high-boiling alcohols. Other fine particle size materials characterized as hydrophobic may be as effective as the hydrophobic silicas since it is not so much the chemical composition of the fine particle size coating composition which is critical to this process but rather their physical properties. Generally, the coating material must be substantially insoluble in water, have a primary particle size of about 0.01 microns to about 0.04 microns, and have a surface area of about 90 to about 130 square meters per gram.

As is conventional in the art, the vitamin emulsion or slurry can contain optional additives such as preservatives, emulsifying agents, antioxidants, etc. Preservatives can be added to the vitamin emulsion or slurry at a level of about 0.4 percent by weight to about 0.6 percent by weight based upon the weight of the emulsion or slurry. Suitable preservatives are known in the art and can be, for example, such preservatives as the alkali metal benzoates and sorbic acid. Such preservatives may be particularly necessary where hydrolyzed gelatin is utilized as the encapsulation agent in order to prevent microbiological growth during preparation and holding of the emulsion or dispersion prior to spray-drying.

In addition, conventional tableting lubricants can be added to the vitamin emulsion or dispersion prior to spray-drying. It is more conventional to add these lubricants to the vitamin powders prior to the tableting operation. Such conventional lubricants as calcium stearate, stearic acid or magnesium stearate, or mixtures thereof, can be used. Any of the aforementioned lubricants can also be used in combination with talc or corn starch to provide additional advantageous properties upon use of the vitamin powders of the invention directly in the preparation of tablets. Generally, about 0.25 percent to about 10 percent by weight of lubricant based upon the dry weight of the vitamin powder of the invention is utilized.

The vitamin powders of the invention are readily processed to provide tablets on conventional tableting equipment dry direct compression, that is, without any granulating step prior thereto. Because of the superior properties of the vitamin powders of the invention will respect to flowability and non-caking at a temperature of 37° C. and 65 percent relative humidity, the vitamin compositions of the invention provide greatly improved process characteristics when utilized to prepare tablets by conventional techniques utilizing conventional tableting equipment.

In addition to the required ingredients of the vitamin powders of the invention previously described, there can be added to the emulsion or dispersion prior to spray-drying other adjuvents and excipients normally found in vitamin tablets. These include, for example, sweetening agents such as saccharin, sodium succaryl, other flavoring agents and coloring agents. The proportion of such agents will be sufficient to serve the intended purpose.

The improved flowability characteristics of the vitamin powders of this invention were unexpected. The coating of partially spray-dried encapsulated vitamin by the introduction into the spray chamber of ultra-fine absorbents such as silicic acid, silicon dioxide or various silicates is known. However, it was not anticipated that the introduction into the spray chamber of an ultra-fine particle size hydrophobic silica would provide the unexpected, substantially improved flow properties of the vitamin powder obtained thereby, as compared with those vitamin powders of the prior art. It was especially unexpected that the substantially improved flow properties would be obtained in a powder which is non-agglomerated, as compared to those vitamin powders of the prior art which are intentionally prepared as agglomerated powders in order to improve flow properties by this means. Generally the vitamin powders of the invention contain a hydrophobic silica coating in the amount by weight of about 0.2 percent to about 2.0 percent, preferably about 0.5 percent to about 1.5 percent, and most preferably about 0.8 percent to about 1.2 percent, all based upon the weight of said powders.

In addition to the uses of the vitamin powder of the invention in the preparation of tablets by direct compression, the non-agglomerated vitamin products of the invention can be used in other ways such as, for example, directly in food premixes, in dry, water-dispersible preparations to be used as diluents for bulk feed. The vitamin powders of the invention are non-agglomerated, non-electrostatic and non-hydroscopic powders having a moisture content of about 1 to about 5 percent by weight and a bulk density of about 0.6 to about 0.9 grams per cubic centimeter. The non-agglomerated powders of the invention have the following composition on a dry basis:

Vitamin—about 45 to about 60 percent by weight, preferably about 48 percent to about 55 percent by weight, Encapsulating agent—about 10 to about 60 percent by weight, preferably about 15 percent to about 50 percent by weight, Water-insoluble carrier—optionally about 2 to about 18 percent by weight and preferably about 3 percent to about 12 percent by weight, Hydrophobic silica—about 0.2 to about 2 percent by weight, preferably about 0.5 percent to about 1.5 percent by weight.

The following test procedures were utilized in evaluating the properties of the vitamin powders of the invention.

The caking tendency of the vitamin powders was evaluated after allowing the powders to stand over a period of 45 hours at a temperature of 37° C. and 65 percent relative humidity.

The bulk density of the powders of the invention was determined by adding to a 1000 ml graduate sufficient vitamin powder to fill the graduate to the top mark. The graduated cylinder was then weighed to the nearest tenth of a gram, the cylinder was then tapped 10 to 20 times on a bench top and the resultant volume recorded to the nearest milliliter. The bulk density in grams per cubic centimeter or pounds per cubic foot was calculated from these measurements.

The flowability of the powders of the invention was evaluated utilizing a device sold under the trademark FLODEX ®, Model 211. This device is covered by foreign and U.S. patents to Dow-Lepetit. In operation, a 50 gram sample is utilized to fill a receptacle cylinder to within a centimeter from the top of the cylinder. Loading is accomplished through a stainless steel funnel, the output side of which is adjusted to be centered over the stainless steel cylinder assembly. Various flow discs which form the bottom of the cylinder are used to evaluate flowability, the flowability being determined by the diameter of the smallest circular hole through which the sample will pass. The flowability is reported as the reciprocal of the diameter in millimeters times 1,000 of the smallest hole through which the powder passes. The maximum flowability is obtained in this test utilizing a flow disc having a four millimeter diameter orifice. The flow obtained is reported as equal to or exceeding a value of 250.

The following examples illustrate the various aspects of the invention but are not intended to limits its scope. Where not otherwise specified throughout this specification and claims, temperatures are given in degrees centigrade and parts, percentages and proportions are by weight.

EXAMPLE 1

This example illustrates a procedure for the preparation of a free-flowing, non-agglomerated, static-free riboflavin powder containing over 50 percent by weight of riboflavin in the dry powder, which also contains about 2 to about 4 percent moisture.

In a five-gallon tank heated utilizing a hot plate, 19.9 parts by weight of a water-soluble corn starch identified as a maltodextrin and sold under the trade name "Maltrin" M040 by the Grain Processing Corporation were added with stirring to 42.8 parts by weight of water maintained at a temperature of 60° C. while constantly stirring the mixture. Thereafter, 31.3 parts by weight of a commercially available riboflavin powder having a purity of about 93 percent by weight were added to the mixture to yield a muddy-yellow suspension of riboflavin. Calcium sulfate dihydrate in the amount of 6 parts by weight was next added and dispersed in the mixture.

Utilizing a laboratory size spray-drying apparatus, having a variable speed atomizing wheel, feed tanks, pump and silica screw feeder, the previously prepared riboflavin suspension was metered to the atomizing wheel operated at about 23,000 rpm. A silica cloud was maintained within the spray-dryer by screw feeding a hydrophobic synthetic silica, sold under the trademark SIPERNAT ® D17, so as to provide a coating on the spray-dried particles. This silica coating constitutes about 1 to 2 percent by weight of the total weight of the particles.

The resulting riboflavin powder is an orange-brown, free-flowing, non-agglomerated, static-free powder having a bulk density of about 0.7 to about 0.8 grams per cubic centimeter and a hygroscopicity of 3.4 percent by weight after exposure to 65 percent relative humidity at a temperature of 37° C. for a period of 45 hours. No caking was observed under these conditions. The flowability index, as measured by the FLODEX method, was found to be equal to or greater than 250 which is indicative of excellent flowability. An index of 250 is the highest measurable level of flowability using this method.

EXAMPLE 2

(Control, forming no part of this invention)

Following the procedure of Example 1, a spray-dried riboflavin powder was prepared. As a substitute for the hydrophobic silica utilized in Example 1, a hydrophilic silica was utilized. The silica was a type sold under the trademark AEROSIL ®200. The resulting spray-dried riboflavin powder obtained was a brown, free-flowing, non-agglomerated, static-free powder having a bulk density of 0.65 to about 0.77 grams per cubic centimeter and a moisture content of 2.74 percent by weight. The hygroscopicity was 3.5 percent by weight after exposure to a relative humidity of 65 percent and a temperature of 37° C. for a period of 45 hours. No caking was observed under these conditions. Evaluation for flowability utilizing the FLODEX method described above provided a flow index of 63.

EXAMPLE 3

(Control, forming no part of this invention)

The procedure of Example 1 was followed utilizing the following proportions of ingredients in the preparation of the suspension of riboflavin:

Riboflavin—about 93 percent by weight purity—32.3 parts by weight,
Maltodextrin—20.07 parts by weight,
Calcium sulfate dihydrate—4.76 parts by weight,
Water—42.8 parts by weight.

In spray-drying the above suspension of riboflavin, the maintenance of a silica cloud within the spray dryer, as shown in Examples 1 and 2, was not utilized. The resulting spray-dried riboflavin powder is a brown, non-agglomerated, static-free powder having a bulk density of 0.6 to 0.73 grams per cubic centimeter, a hygroscopicity of 3.4 percent by weight after exposure to a 65 percent relative humidity at a temperature of 37° C. for a period of 45 hours. It is noted that the powder solidified subsequent to exposure under these temperatures and humidity conditions, as compared to the riboflavin powders of Examples 1 and 2 in which no solidification took place. The flowability measured using the FLODEX method showed an index of 71.

EXAMPLE 4

In order to evaluate the suitability of the riboflavin powder of Example 1 for tableting without further granulation, the following mixture was prepared for use in a tableting machine identified as a Stokes D-2 rotary press tableting machine:

Riboflavin powder of Example 1—94 percent by weight,
Microcrystalline cellulose sold under the trademark AVICEL—5 percent by weight,
Magnesium stearate—1 percent by weight.

Tablets were obtained of excellent appearance.

While this invention has been described with reference to certain specific embodiments, it will be recognized by those skilled in the art that many variations are possible without departing from the scope and spirit of the invention and it will be understood that it is intended to cover all changes and modification to the invention disclosed herein for the purposes of illustration which do not constitute departures from the spirit and scope of the invention.

The embodiments of the invention in which an exclusive property or privilege is claimed are defined as follows:

1. In a process for preparing coated, non-agglomerated, spray-dried vitamin powders suitable for the preparation of tablets by direct compression comprising:
   A. spraying into a spray-dryer chamber droplets of a composition containing a vitamin present as a dispersion, solution, or as an emulsion in an aqueous medium containing an encapsulating agent and wherein a water-insoluble carrier is optionally present in said aqueous medium, to produce a spray-dried powder which is dried in the presence of a dry particulate absorbent material, the improvement comprising:
   B. metering into said chamber, in a concentration of about 0.2 to about 2 percent by weight, based upon the weight of said spray-dried vitamin powder, a hydrophobic silica.

2. The process of claim 1 wherein said vitamin is present as a dispersion in said aqueous medium containing said encapsulating agent comprising a water-soluble starch, dextrin, corn syrup, or mixtures thereof.

3. The process of claim 2 wherein said water-insoluble carrier is present and selected from the group consisting of calcium sulfate, dicalcium phosphate, oyster shell flour, corn starch, rice starch, and mixtures thereof.

4. The process of claim 3 wherein said vitamin is riboflavin and said dextrin is maltodextrin.

5. The process of claim 4 wherein said non-agglomerated powder has the following composition on a dry basis:
   riboflavin—about 45 to about 60 percent by weight,
   encapsulating agent—about 20 to about 52 percent by weight,
   calcium sulfate dihydrate—about 2 to about 18 percent by weight,
   hydrophobic silica—about 0.2 to about 2 percent by weight.

6. A spray-dried, free-flowing, non-agglomerated, non-caking, non-hygroscopic vitamin powder composition comprising in percent by weight based upon the total weight of said powder, about 45 to about 60 percent vitamin, about 10 to about 60 percent of an encapsulating agent, optionally about 2 to about 18 percent of a water-insoluble, carrier, and about 0.2 to about 2 percent of a hydrophobic silica.

7. The composition of claim 6 wherein said encapsulating agent is selected from the group consisting of a water-soluble starch, dextrin, corn syrup and mixtures thereof.

8. The composition of claim 7 wherein said dextrin is maltodextrin.

9. The composition of claim 7 wherein said water-insoluble carrier is present and selected from the group consisting of calcium sulfate, dicalcium phosphate, oyster shell flour, corn starch, rice starch, and mixtures thereof.

10. The composition of claim 9 wherein said vitamin is riboflavin and said powder is coated with about 0.5 to about 1.5 percent of said hydrophobic silica.

* * * * *